(12) United States Patent
Wieters et al.

(10) Patent No.: US 12,147,024 B2
(45) Date of Patent: Nov. 19, 2024

(54) DEFLECTION PRISM ASSEMBLY FOR AN ENDOSCOPE HAVING A LATERAL VIEWING DIRECTION, ENDOSCOPE HAVING A LATERAL VIEWING DIRECTION AND METHOD FOR ASSEMBLING A DEFLECTION PRISM ASSEMBLY

(71) Applicant: OLYMPUS WINTER & IBE GMBH, Hamburg (DE)

(72) Inventors: Martin Wieters, Barsbuettel (DE); Alrun Thuemen, Hamburg (DE)

(73) Assignee: OLYMPUS WINTER & IBE GMBH, Hamburg (DE)

( * ) Notice: Subject to any disclaimer, the term of this patent is extended or adjusted under 35 U.S.C. 154(b) by 55 days.

(21) Appl. No.: 18/199,080

(22) Filed: May 18, 2023

(65) Prior Publication Data

US 2023/0288693 A1  Sep. 14, 2023

Related U.S. Application Data

(63) Continuation of application No. 17/132,003, filed on Dec. 23, 2020, now Pat. No. 11,693,227, which is a
(Continued)

(30) Foreign Application Priority Data

Jun. 25, 2018 (DE) ............ 10 2018 115 238.8

(51) Int. Cl.
*G02B 23/24* (2006.01)
*G02B 5/04* (2006.01)
*A61B 1/00* (2006.01)

(52) U.S. Cl.
CPC ............ *G02B 23/243* (2013.01); *G02B 5/04* (2013.01); *A61B 1/00096* (2013.01)

(58) Field of Classification Search
None
See application file for complete search history.

(56) References Cited

U.S. PATENT DOCUMENTS

| 4,328,185 A | 5/1982 | Reasons et al. |
| 2004/0070820 A1 | 4/2004 | Nishimura |

(Continued)

FOREIGN PATENT DOCUMENTS

| CN | 202583594 U | 12/2012 |
| CN | 205386130 U * | 7/2016 |

(Continued)

OTHER PUBLICATIONS

International Search Report dated Sep. 20, 2019 received in PCT/EP2019/065137.
(Continued)

*Primary Examiner* — Shadan E Haghani
(74) *Attorney, Agent, or Firm* — Scully, Scott, Murphy & Presser, P.C.

(57) ABSTRACT

A deflection prism assembly for an endoscope having a lateral viewing direction. The deflection prism assembly including: a prism holder; a deflection prism which is received in the prism holder; and at least one electrical heating element for heating the deflection prism. The prism holder includes a reception component and an adjustment component. The deflection prism is attached to the reception component and the adjustment component provides a stop for the deflection prism in an axial direction. Wherein the at least one electrical heating element being disposed in or on the reception component; and the at least one electrical heating element at least partially extending in one or more of a circumferential direction or longitudinal direction of the reception component.

14 Claims, 6 Drawing Sheets

Related U.S. Application Data continuation of application No. PCT/EP2019/065137, filed on Jun. 11, 2019.

(56) References Cited

U.S. PATENT DOCUMENTS

| | | | |
|---|---|---|---|
| 2007/0273986 | A1 | 11/2007 | Kajita |
| 2012/0078049 | A1 | 3/2012 | Pauli et al. |
| 2012/0182458 | A1* | 7/2012 | Ishii ..................... G03B 17/17 359/833 |
| 2014/0288369 | A1* | 9/2014 | Henley .............. A61B 1/00179 600/109 |
| 2014/0288370 | A1* | 9/2014 | Jungbauer .......... A61B 1/00101 600/112 |
| 2017/0188802 | A1* | 7/2017 | Lawrence ............ A61B 1/0607 |
| 2017/0332894 | A1* | 11/2017 | Fujii .................. A61B 1/00188 |

FOREIGN PATENT DOCUMENTS

| | | |
|---|---|---|
| DE | 24 58 306 A1 | 6/1975 |
| DE | 10 2013 217 500 A1 | 3/2015 |
| DE | 10 2015 101 624 A1 | 8/2016 |
| DE | 10 2017 124 593 A1 | 4/2019 |
| EP | 0 978 251 A1 | 2/2000 |
| EP | 1164800 A2 * 12/2001 ......... H04N 1/00978 |
| EP | 2 474 849 A1 | 7/2012 |
| EP | 2 777 481 A1 | 9/2014 |
| EP | 3 135 181 A1 | 3/2017 |
| JP | S63-208017 A | 8/1988 |
| JP | H06-35301 Y2 | 9/1994 |
| JP | 2000-094284 A | 4/2000 |
| JP | 5505578 B1 | 5/2014 |

OTHER PUBLICATIONS

US Office Action dated Mar. 10, 2022 received in U.S. Appl. No. 17/132,003.

US Office Action dated Sep. 9, 2022 received in U.S. Appl. No. 17/132,003.

US Office Action dated Dec. 2, 2022 received in U.S. Appl. No. 17/132,003.

* cited by examiner

DEFLECTION PRISM ASSEMBLY FOR AN ENDOSCOPE HAVING A LATERAL VIEWING DIRECTION, ENDOSCOPE HAVING A LATERAL VIEWING DIRECTION AND METHOD FOR ASSEMBLING A DEFLECTION PRISM ASSEMBLY

CROSS-REFERENCE TO RELATED APPLICATION

The present application is a Continuation of U.S. patent application Ser. No. 17/132,003, filed on Dec. 23, 2020, which is a Continuation of PCT/EP2019/065137 filed on Jun. 11, 2019, which is based upon and claims the benefit to DE 10 2018 115 238.8 filed on Jun. 25, 2018, the entire contents of each of which are incorporated herein by reference.

BACKGROUND

Field

The present disclosure relates to a deflection prism assembly for an endoscope having a lateral viewing direction, comprising a prism holder and a deflection prism, which is received in the prism holder, wherein the deflection prism is produced from a glass. Moreover, the present disclosure relates to an endoscope having a lateral viewing direction and a method for assembling a deflection prism assembly.

Prior Art

In the medical field, both endoscopes which look forwards frontally and endoscopes having a viewing direction which deviates by an angle greater than 0° from said frontal viewing direction are deployed. In the latter case, these are referred to as endoscopes having a lateral viewing direction.

Distal deflection prisms are frequently deployed in endoscopes having a lateral viewing direction. The distal deflection prisms are mostly composed of multiple sub-prisms and serve to deflect diagonally incident light such that it runs parallel to a longitudinal axis of the endoscope shaft.

Deflection prisms have to satisfy a plurality of requirements. A deflection prism should be embodied such that light from as large as possible a field of view can enter the endoscope and be forwarded into the optical system of the endoscope. Simultaneously, the dimensions of the deflection prism must be small enough that it can be arranged and attached in the endoscope shaft. In addition, the deflection prism must be aligned in the endoscope such that incident light bundles are forwarded in the manner provided. If the deflection prism is not correctly aligned, image errors or a deterioration of the image quality can occur.

Conventionally, a lateral face of the deflection prism is completely surrounded by a cylinder-shaped prism holder. This prism holder receives the deflection prism, attaches it and serves as a reference system for aligning the deflection prism in the endoscope. It is disadvantageous that a cylinder-shaped prism holder of this type limits the maximum dimensions of the deflection prism in the radial direction.

Document DE 10 2017 124 593 of the applicant Olympus Winter & Ibe GmbH, Hamburg, which has not previously been published, discloses a deflection prism assembly which comprises a deflection prism and a prism holder. The lateral face of the deflection prism is only surrounded by the prism holder in certain regions so that the deflection prism can be embodied larger in the radial direction in the region which is not enclosed by the prism holder. In this way, more light travels through the deflection prism into the optical system of the endoscope.

In order to be able to exactly receive the deflection prism with respect to the optical axis of the endoscope, the prism holder must be manufactured exactly. The prism holder must therefore be produced from a material that allows an exact production and processing with respect to its dimensions. Metals, e.g. brass or austenitic steel, are suitable for this purpose.

It is true that these materials make it possible to manufacture the prism holder exactly, however it is disadvantageous that the thermal expansion coefficient of such a metal differs significantly from the thermal expansion coefficient of the glass, from which the deflection prism is manufactured. This can lead to technical difficulties during the attachment of the deflection prism in the prism holder. The high-strength and temperature-stable adhesive deployed to attach the deflection prism must be vigorously heated during curing. Due to the different thermal expansion coefficients, tensions occur between the deflection prism and the prism holder during this process, which can lead to a fracture of the deflection prism.

FIG. 2 shows a schematically simplified representation of a longitudinal section through a deflection prism assembly 13, as it is frequently used in the prior art.

The deflection prism 16 comprises three sub-prisms 16a, 16b, 16c which deflect incident light bundles in the direction of the longitudinal axis of an endoscope shaft 4. This is shown using the example of the beam path 19. Incident light bundles along said beam path 19 enter through the inlet lens 17, which in this embodiment is likewise configured as the inlet window 10, into the endoscope 2. The light bundles are subsequently reflected twice in the deflection prism 16 and forwarded through an outlet lens 18 into an optical system (not shown) of the endoscope 2.

The deflection prism 16 comprises a light inlet face 62, a light outlet face 64 and a lateral face 66 which extends between the light inlet face 62 and the light outlet face 64. The lateral face is cylindrical. In the embodiment shown in FIG. 2, the lateral face 66 of the deflection prism 16 is completely enveloped by a substantially cylinder-shaped prism holder 14. As a result of this complete enveloping, the deflection prism 16 can indeed be aligned and attached with little outlay in the prism holder 14, but the dimensions of the deflection prism 16 are limited by the prism holder 14.

FIG. 3 shows a further embodiment of a deflection prism assembly 23 as is shown, for example, in document DE 10 2017 124 593. In this embodiment of the deflection prism assembly 23, the prism holder 24 only encloses the deflection prism 26 in certain regions or in sections. As a result, the deflection prism 26 can be configured larger in the radial direction in the distal upper region. The field of view of an endoscope 2 having such a deflection prism assembly 23 is therefore larger than the field of view of an endoscope 2 having a deflection prism assembly 13, as shown by way of example in FIG. 2.

Since the deflection prism 26 in the embodiment shown in FIG. 3 is not, however, enveloped in a circumferential manner by the prism holder 24, the deflection prism 26 has to be attached in the deflection prism assembly 23 with a high-strength and temperature-stable adhesive. In order to cure an adhesive of this type, high temperatures are necessary. At these high temperatures, mechanical stresses can occur between the deflection prism 26 produced from a glass and the prism holder 24 produced from a metal, for example a steel alloy.

SUMMARY

An object is to provide a deflection prism assembly, an endoscope having a lateral viewing direction and a method for assembling a deflection prism assembly, with which both a high optical quality and reliable and efficient manufacture of the deflection prism assembly and of the endoscope can be achieved.

Such object can be solved by a deflection prism assembly for an endoscope having a lateral viewing direction, comprising a prism holder and a deflection prism, which is received in the prism holder, wherein the deflection prism is produced from a glass, the prism holder comprises a reception component and an adjustment component, wherein the reception component is produced from a ceramic and the adjustment component is produced from a metal, wherein the deflection prism is attached to the reception component and the adjustment component provides a stop for the deflection prism in an axial direction.

The prism holder comprises two components: a reception component and an adjustment component. The reception component is configured to receive the deflection prism and is produced from a ceramic. Said ceramic can be selected such that the thermal expansion coefficient of the ceramic substantially coincides with the thermal expansion coefficient of the glass, from which the deflection prism is produced. Even if it is not necessary or possible for the thermal expansion coefficients to correspond exactly, the ceramic can be, however, selected such that its thermal expansion coefficient differs from the thermal expansion coefficient of the glass by less than a predefined threshold value. This can prevent the deflection prism tensing mechanically with respect to the reception component when the deflection prism assembly is heated. The probability of damage to the deflection prism group can thus be substantially reduced during this process.

The adjustment component serves to axially align the deflection prism. It provides a stop for the deflection prism, on which stop the deflection prism is brought to rest, indirectly or directly. If the deflection prism is brought to rest directly, it is in direct contact with the stop. The material of the adjustment component is a metal. A component made of a metal can be produced more precisely than a component made of ceramic. The adjustment component can be reworked by cutting. Thus, a high precision can be achieved during the alignment of the deflection prism.

A mask can be arranged between the deflection prism and the stop, which mask can act as a spacer. In such a case, the deflection prism can be brought to rest indirectly on the stop.

Within the context of the present description, the term "axial direction" is understood to be a direction which runs parallel to a longitudinal axial direction of the endoscope shaft, to which the deflection prism assembly is attached. An "axial alignment" is accordingly an alignment of a component in said axial direction.

The adjustment component, which is a part of the prism holder, can allow the deflection prism to be precisely aligned in the deflection prism assembly. As a result, a high optical quality of the deflection prism assembly and of an endoscope having such a deflection prism assembly is attained.

According to an embodiment, the adjustment component can be produced from a non-ferromagnetic metal, such as a non-ferromagnetic steel alloy. For example, the adjustment component can be produced from the steel alloy having the material number 1.4305. Magnetic actuators, with which the axial position of optical elements can be modified, for example, can be arranged in optical systems of endoscopes. The production of the adjustment component from a non-ferromagnetic metal can prevent the magnetic actuators being adversely affected by the adjustment component.

At least one electrical heating element for heating the deflection prism assembly can be present in or on the reception component or integrated into the reception component, wherein the electrical heating element can run at least in sections within the reception component.

The electrical heating element can be arranged on a surface of the reception component. The heating element can be arranged on an outer side which faces away from the deflection prism assembly. Two different embodiments can be provided: a first embodiment in which the electrical heating element can be integrated into the reception component, and a second embodiment in which the electrical heating element can be arranged on a surface of the reception component.

The integration of a heating element into the reception component or the arranging of the electrical heating element on the reception component can provide warming of the deflection prism assembly, if necessary. During the practical deployment of the endoscope, optical faces can mist up, for example the inlet window or the optical faces of the deflection prism assembly, as a result of which the image quality is considerably restricted. By warming the deflection prism assembly, the optical faces can be freed from the condensation so that there is a clear view again.

Producing the reception component from a ceramic to act as an electrical insulator is exploited during the arrangement of the electrical heating element. Electrical insulation between the electrical heating element and the reception component can be dispensed with.

The heating element can be a structure made of a conductive material, which structure can be printed onto the reception component or, thanks to the multilayer construction of the ceramic, can be integrated into the structural body produced from the ceramic. In order to establish an electrical contact with this heating element, a thin printed circuit board can be used.

When such a reception component made of ceramic and a heating element of this type are used, the deflection prism can be embodied to be larger than is the case with a prism holder which is completely produced from a conductive metal. Installation space can of course be saved by dispensing with the electrical insulation.

At least one temperature sensor can be present in or on the reception component.

Such a temperature sensor can be a thermistor which is configured as a negative temperature coefficient thermistor or as a positive temperature coefficient thermistor. The temperature at the location of the deflection prism assembly can be monitored by the temperature sensor. The temperature sensor can be deployed in conjunction with an electrical heating element, in order to monitor the warming attained by the electrical heating element. As is also the case with the electrical heating element, the temperature sensor, due to the production of the reception component from a ceramic, without using additional insulation, can be printed onto the surface of the reception component or integrated into the reception component.

The adjustment component can provide reference points for the radial alignment of the deflection prism.

Within the context of the present specification, the term "radial direction" is understood to be a direction which runs vertically to the longitudinal axial direction of the endoscope shaft, to which the deflection prism assembly is attached. A "radial alignment" is an alignment in this radial direction.

Due to the reference points of the adjustment component, the radial alignment of the deflection prism can also be performed exactly due to the precise production of the adjustment component. The reference points can be configured to interact with an adjustment device which lies in contact with at least three, such as four, regions of the lateral face of the deflection prism. These regions can be points. For example, it is provided that such an adjustment device, viewed in a plane vertical to the longitudinal axial direction, can act upon points at 9 o'clock, twelve o'clock and three o'clock. If an adjustment device which acts upon four points is provided, these are for example the points spaced apart by 90° at twelve o'clock, three o'clock, six o'clock and nine o'clock.

Due to the use of an adjustment device of this type, the adjustment component, which can be precisely manufactured and aligned, can be used as a reference system for the radial alignment of the deflection prism.

According to a further embodiment, the deflection prism can have a light outlet face and an opposite light inlet face arranged diagonally thereto, between which a lateral face extends, wherein the prism holder receives the deflection prism in such a way that the prism holder simply surrounds the lateral face of the deflection prism in sections, such as does not surround it completely. The prism holder can be, in other words, embodied such that it simply rests on the lateral face of the deflection prism in sections, that is to say it does not surround a part of the lateral face.

The prism holder can lie in contact with the lateral face of the prism in a first region, wherein a second region of the deflection prism radially opposite the first region is not surrounded by the prism holder.

Such an embodiment of the prism holder offers, for example, a simplified assembly while simultaneously improving the optical imaging quality. The effective cross-sectional area of the prism for the light entry can, moreover, be increased without the installation space of the entire unit increasing. The provision of an adjustment component and a reception component simultaneously prevents tensioning of the deflection prism occurring during curing of an adhesive between the deflection prism and the prism holder. Consequently, a high optical quality is achieved at the same time as reliably and efficiently assembling the deflection prism assembly.

The light outlet face of the deflection prism can lie in contact with the stop of the adjustment component. The deflection prism can lie in contact with the stop of the adjustment component with a stop face which is oriented parallel to the light outlet face. The reception component can surround exclusively the lateral face of the deflection prism in certain regions or in sections, as previously described; by contrast, the adjustment component does not have to surround the lateral face of the deflection prism in any region since it does not have to come into contact with the lateral face of the deflection prism. In this way, it is ensured that a tensioning does not occur between the deflection prism and the adjustment component when the deflection prism assembly is heated.

The deflection prism can be exclusively attached to the reception component, such as by means of an adhesive. This measure can ensure that the deflection prism is securely attached in the deflection prism assembly and, simultaneously, the attachment does not adversely affect the alignment of the deflection prism. Such an adverse effect would occur, for example, if an adhesive layer were to form between the deflection prism and the stop.

At least one adhesive gap can be present between the deflection prism and the reception component, wherein the at least one adhesive gap has a gap width which is large enough that, taking account of manufacturing tolerances, the deflection prism does not lie in contact with the reception component at any point.

The adhesive gap can be filled with an adhesive. Providing an adhesive gap ensures that the deflection prism is, on the one hand, securely attached in the deflection prism assembly and, on the other hand, the deflection prism does not lie in contact with the reception component at any point. In this way it is ensured that, despite the fluctuations which can occur with the dimensions of the reception component by virtue of the fact that the reception component is produced from a ceramic, the deflection prism does not touch the reception component at any point. Thus, the deflection prism can be exclusively aligned radially and axially by the stop and the reference points of the adjustment component.

The reception component can be attached to the adjustment component, such as by means of an adhesive.

The reception component can be attached and, can also be aligned by means of the adjustment component. Due to the precise production of the adjustment component, this constitutes a suitable reference system not only for the deflection prism but also for the reception component. The adjustment component can comprise a guide which is configured as an axial and/or radial slide bearing. The adjustment component can be connected to the optical system of an endoscope by means of said guide. The slide bearings can allow a rotation of the deflection prism assembly in order to modify the viewing direction of the endoscope as well as an adjustment of the distance between the deflection prism and the optical system.

Such object can also be solved by an endoscope having a lateral viewing direction, comprising a deflection prism assembly according to any one of the previously indicated embodiments.

Such object can also be solved by a method for assembling a deflection prism assembly according to any one of the previously indicated embodiments, wherein the method comprises: attaching the adjustment component to an optical system of an endoscope, fitting the reception component onto the adjustment component and attaching the reception component to the adjustment component, inserting the deflection prism into the prism holder, axially aligning the deflection prism by bringing the deflection prism to rest on the stop of the adjustment component, and attaching the deflection prism to the reception component.

The endoscope can have a lateral viewing direction and the method for assembling a deflection prism assembly have the same or similar advantages to those which have already been mentioned above with respect to the deflection prism assembly, so repetitions shall be dispensed with.

The axially aligning of the deflection prism can comprise indirectly or directly bringing the deflection prism to rest on the stop of the adjustment component. According to an embodiment, a mask can be arranged on the light outlet face, so that the deflection prism can be indirectly brought to rest on the stop of the adjustment component.

The reception component can be aligned when it is fitted on the adjustment component. In addition, the features of the method can be executed one after the other in the order in which they are enumerated. Consequently, the adjustment component can be first attached to the optical system and precisely aligned with respect to the latter. The reception component can be subsequently positioned on the adjustment component and attached to the latter, such as by means of an adhesive. Since the adjustment component can be configured to align the deflection prism, the alignment of the reception component requires a lower precision than is the case during the alignment of the adjustment component and the deflection prism. Following the attaching of the reception component, the deflection prism can be inserted into the prism holder and can be aligned in the reference system of the adjustment component before the deflection prism is definitively attached to the reception component. The adhesive used to attach the deflection prism can be applied to the reception component prior to inserting the deflection prism and can be cured following the aligning of the deflection prism.

The deflection prism can be radially aligned by means of an adjustment device, wherein the adjustment device can be positioned on the deflection prism assembly, interact with reference points of the adjustment component and lie in contact with at least three regions or points of the lateral face of the deflection prism.

Thanks to the use of an adjustment device of this type, the manufacturing accuracy during the production of the adjustment device can also be utilized for the radial alignment of the deflection prism. An adjustment device of this type can have, for example, a substantially cylindrical form which interacts at one end with the reference points of the adjustment component and, at its other end, can lie in contact with at least three regions of the lateral face of the deflection prism. The reception component can have one or more recesses, through which the adjustment device for aligning the deflection prism engages, in order to lie in contact with the lateral face of the deflection prism.

BRIEF DESCRIPTION OF THE DRAWINGS

Further features will become evident from the description of embodiments, together with the claims and the appended drawings. Embodiments can fulfill individual features or a combination of multiple features.

The embodiments are described below without limiting the general concept of the invention by means of exemplary embodiments with reference to the drawings, wherein reference is expressly made to the drawings regarding all of the details which are not explained in greater detail in the text, wherein.

In the drawings, the same or similar elements and/or parts are, in each case, provided with the same reference numerals so that they are not introduced again in each case.

DETAILED DESCRIPTION

Figure 1:
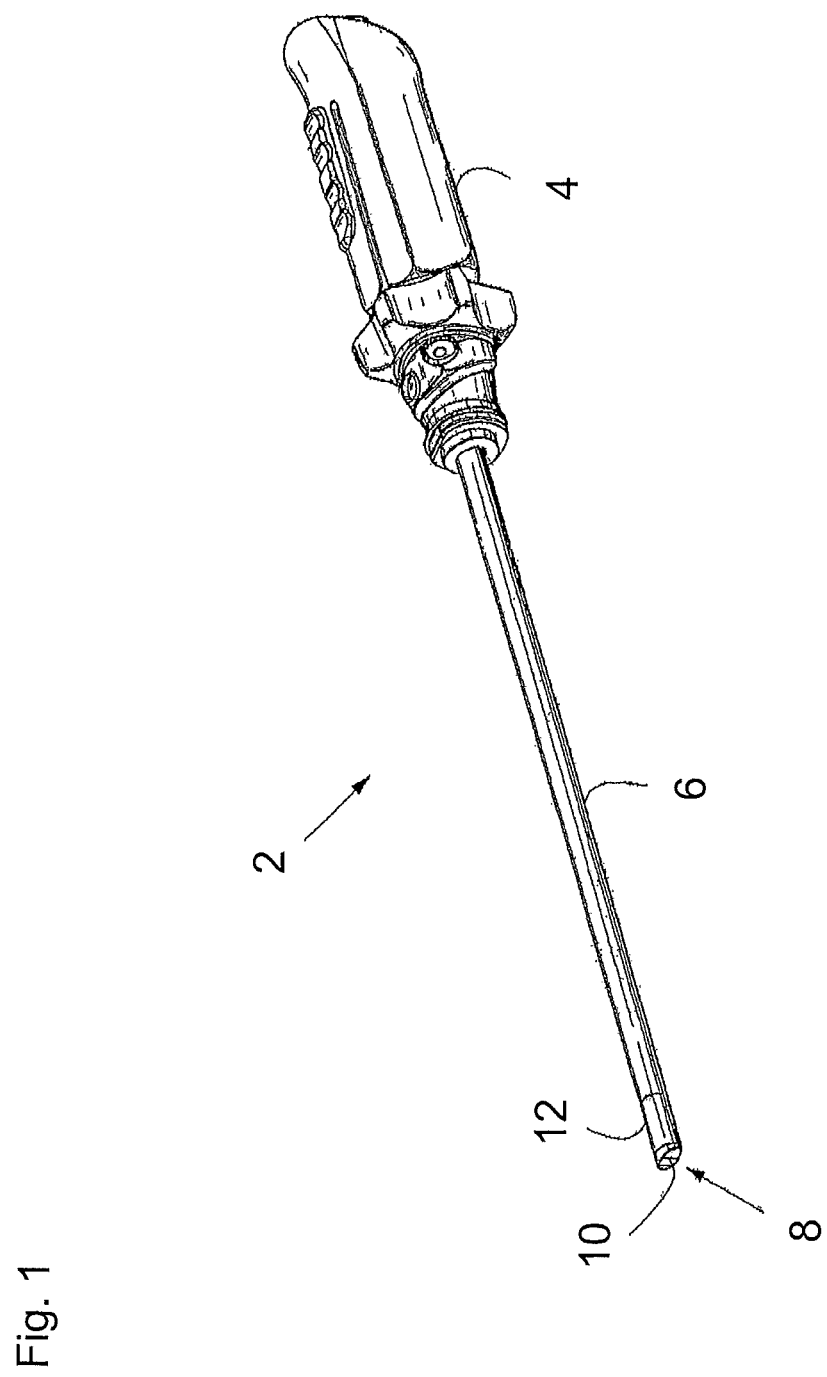
FIG. 1 illustrates a schematically simplified perspective representation of an endoscope.

FIG. 1 shows an endoscope 2 having a lateral viewing direction. At a proximal end of the endoscope 2 there is located a handle 4, to which a shaft 6 or an endoscope shaft is joined. At a distal end 8 of the shaft 6 there is located an inlet window 10, through which light bundles from an observation or operating field located distally in front of the distal end 8 enter the interior of the shaft 6. In a distal end region 12 of the shaft 6, a deflection prism 16 is arranged as part of a deflection prism assembly 13 within the shaft 6.

Figure 2:
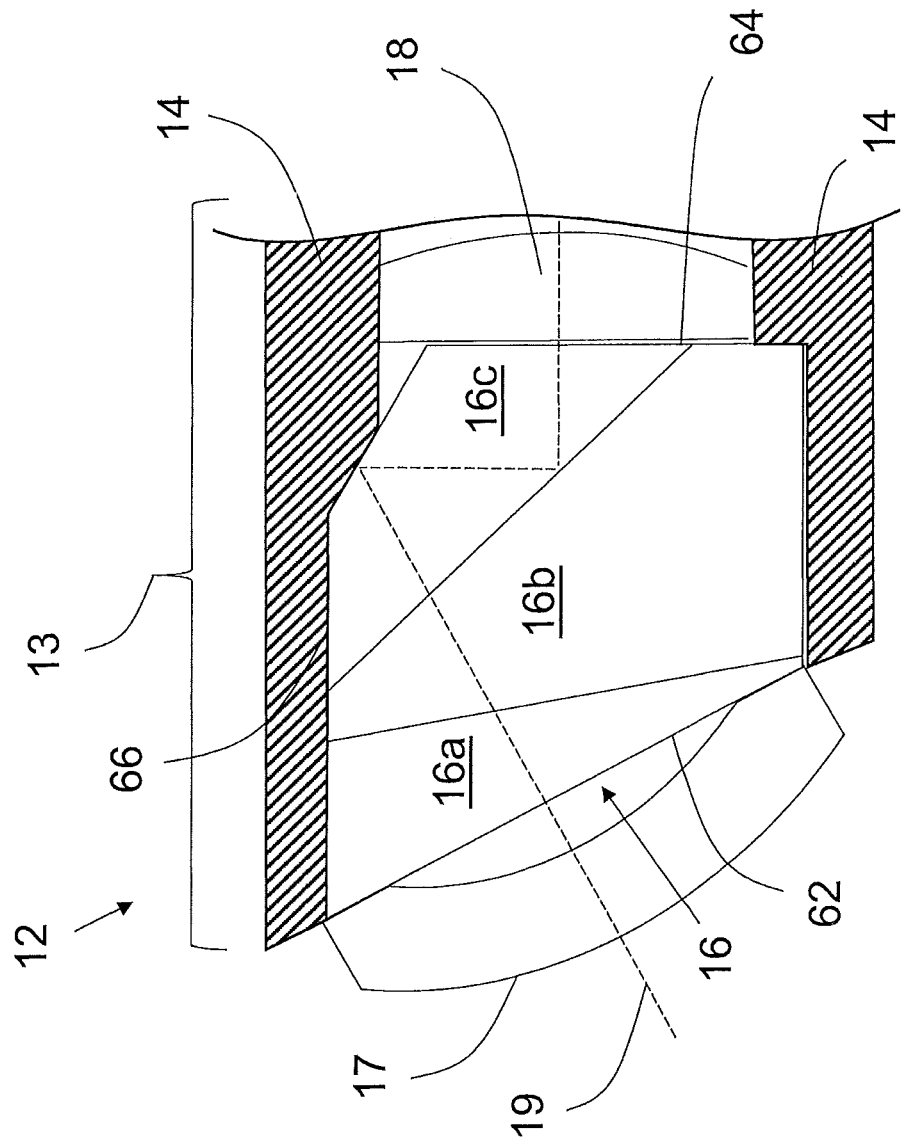
FIG. 2 illustrates a schematically simplified longitudinal section through a deflection prism assembly having an inlet lens, an outlet lens and a prism holder completely enclosing the deflection prism.
Figure 3:
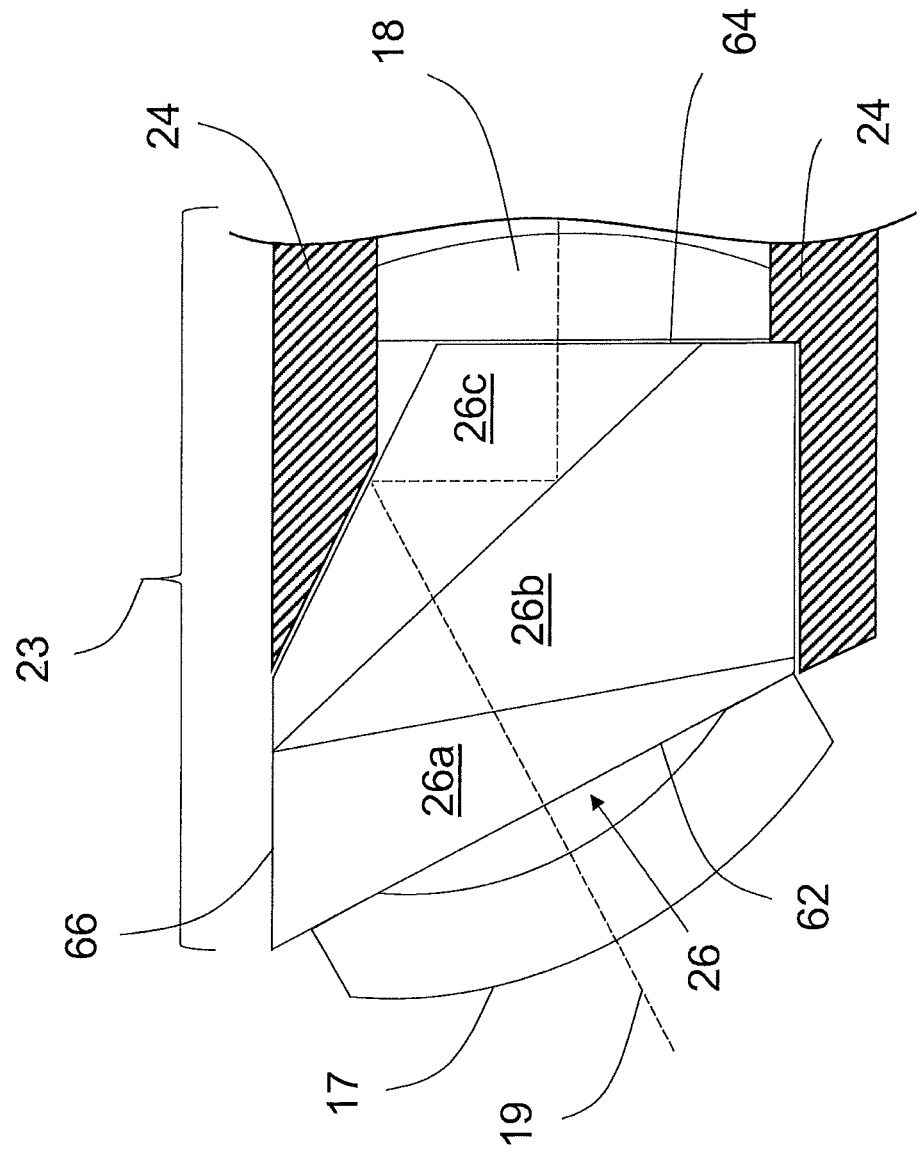
FIG. 3 illustrates a schematically simplified longitudinal section through a deflection prism assembly having an inlet lens, an outlet lens and a prism holder only enclosing the deflection prism in certain regions, which is configured in one piece.
Figure 4:
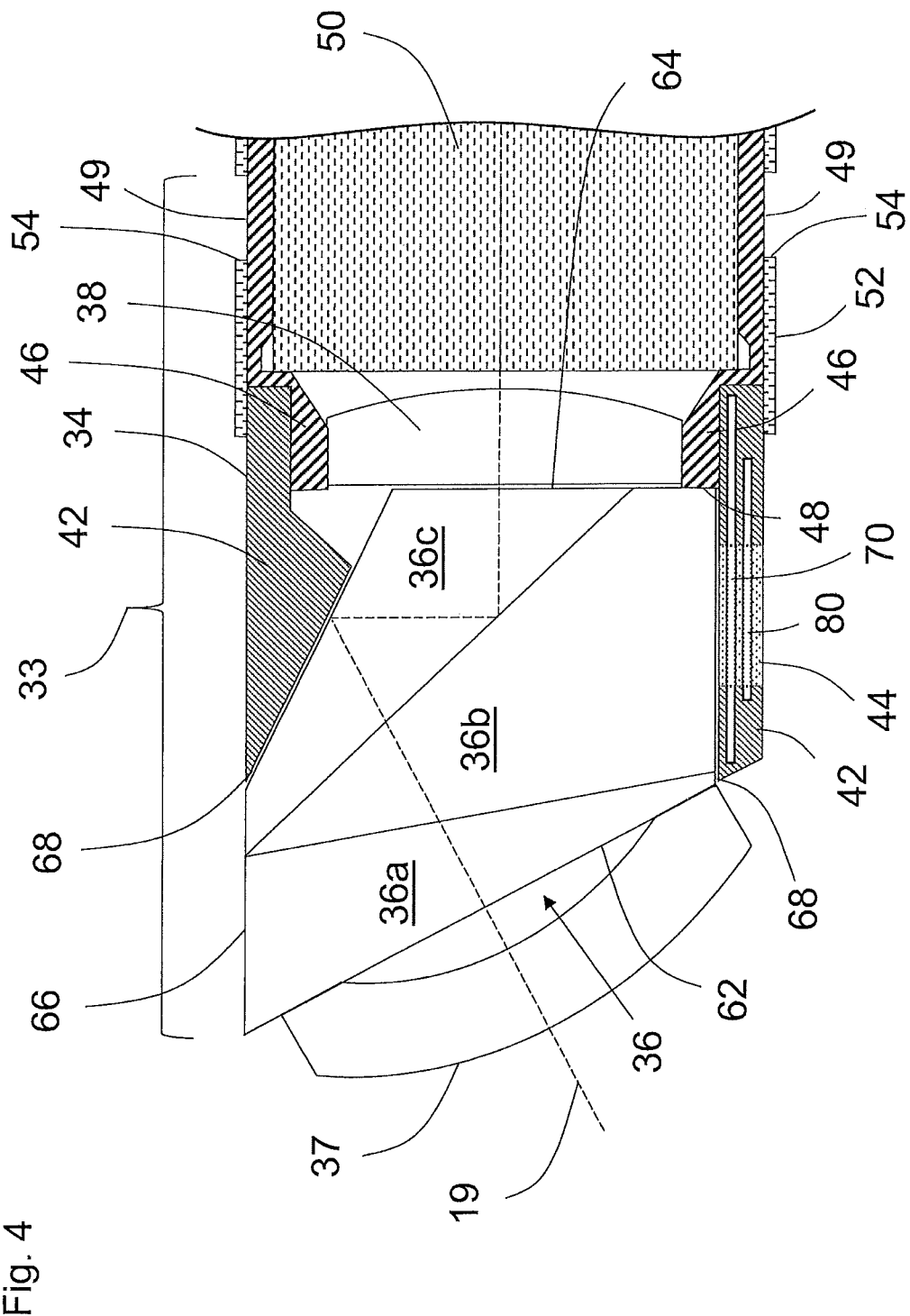
FIG. 4 illustrates a schematically simplified cross-sectional view through a deflection prism assembly having an inlet lens, an outlet lens and a prism holder which comprises a reception component and an adjustment component.

FIG. 4 shows an embodiment of a deflection prism assembly 33 which combines the optical properties of the deflection prism assembly 23 from FIG. 3 with the reliable production of the deflection prism assembly 13 from FIG. 2. The deflection prism assembly 33 comprises the deflection prism 36 and a prism holder 34 which, in turn, comprises a reception component 42 and an adjustment component 46. The inlet lens 37 shown in FIG. 4, the outlet lens 38, the outer casing 52 or the optical system 50 are, by contrast, not part of the deflection prism assembly 33.

The inlet lens 37 and the outlet lens 38 correspond to the inlet lens 17 and the outlet lens 18 from FIGS. 2 and 3. The deflection prism 36 having the sub-prisms 36*a*, 36*b*, 36*c* corresponds to the deflection prism 26 having the sub-prisms 26*a*, 26*b*, 26*c* from FIG. 3. Unlike the prism holder 14 and the prism holder 24, the prism holder 34 in FIG. 4 is, however, composed of two separate components, the reception component 42 (hatching from top right to bottom left) and the adjustment component 46 (hatching from top left to bottom right).

The adjustment component 46 is substantially cylinder-shaped and comprises in its distal region the outlet lens 38. The proximal region of the adjustment component 46 is executed as an axial and radial slide bearing for the optical system 50 of the endoscope 2. This allows a rotation of the deflection prism assembly 33 in order to modify the viewing direction of the endoscope 2 as well as an adjustment of the distance between the deflection prism 36 or respectively the light outlet lens 38 and the optical system 50.

Furthermore, the adjustment component 46 provides a stop 48 for the light outlet face 64 of the deflection prism 36, with which the deflection prism 36 is aligned in the axial direction. To ensure that the alignment of the deflection prism 36 is as exact as possible, the dimensions of the adjustment component 46 have to be precisely observed. For this reason, a metal, for example brass or a steel alloy, is used to produce the adjustment component 46. If the optical system 50 comprises magnetic actuators, the adjustment component 46 is produced from a non-ferromagnetic metal so as not to adversely affect the magnetic actuators.

The reception component 42 is positioned on the adjustment component 46 and, for example, attached to the latter by means of an adhesive. Said reception component 42 substantially corresponds to the region of the prism holder 24 from FIG. 3, which comprises the lateral face 66 of the deflection prism 26. In other words, the deflection prism 36 is exclusively received in the reception component 42 of the prism holder 34 and is also exclusively attached to said reception component 42. An adhesive, which is applied in the adhesive gaps 68 between the deflection prism 36 and the reception component 42, is used for the attaching. Said adhesive gaps 68 are configured so large that, taking account of production-related deviations in the dimensions of the reception component 42, the deflection prism 36 does not lie in contact directly with the reception component 42 at any point.

In contrast to the adjustment component 46, the reception component 42 is produced from a ceramic. Said ceramic has a thermal expansion coefficient which substantially corresponds to the thermal expansion coefficient of the glass used to produce the deflection prism 36. This prevents a tensioning between the deflection prism 36 and the reception component 42 during curing of the adhesive in the adhesive gaps 68. Inaccuracies in the dimensions of the reception component 42, which are caused by the use of the ceramic to produce said component, do not have any influence on the alignment of the deflection prism 36 since the latter, as previously explained, does not lie in contact with the reception component 42 at any point.

The shaft 6 of the endoscope 2 is surrounded by an outer casing 52 up to the distal end region 12. Said outer casing 52 has, in the region of the adjustment component 46, multiple circular recesses 54, for example four recesses 54 which, observed in a plane vertical to the longitudinal axial direction, are arranged at points at twelve o' clock, three o' clock, six o' clock and nine o' clock. In FIG. 4, for illustration reasons, only the recesses 54 at twelve o' clock and six o' clock are shown. Below these recesses 54, the adjustment component 46 provides reference points 49 which interact with an adjustment device which is not shown. Said adjustment device comprises, in addition, the deflection prism 36 on at least three sides, for example at nine o' clock, twelve o' clock and three o' clock so that the deflection prism 36 can be radially aligned in the reference system of the adjustment component 46 by means of the adjustment device. In addition, in the embodiment shown in FIG. 4, the reception component 42 has a recess 44, through which the adjustment device can also be brought to rest from below, that is to say at six o'clock, on the deflection prism 36.

An electrical heating element 70 is integrated in the reception component 42. Since the reception component 42 is manufactured from a ceramic, the provision of an electrical insulating layer between the heating element 70 and the reception component 42 is superfluous. In order to mount the electrical heating element 70, printed circuit boards of an electrically conductive material are mounted on the electrically insulating ceramic. If this happens during the production of the ceramic, the heating element 70 is integrated in this way between multiple layers of the ceramic. The electrical contacting of the heating element 70 happens, for example, through a thin circuit board which is not shown in FIG. 4.

Thanks to the heating element 70, the deflection prism assembly 33 can be warmed up, for example in order to evaporate liquid droplets or respectively condensation which has/have been deposited on the inlet lens 37 or the optical faces of the deflection prism assembly 33.

Furthermore, a temperature sensor 80 is integrated or mounted in the reception component 42. Such a temperature sensor 80 is, for example, a thermistor configured as a negative temperature coefficient thermistor or positive temperature coefficient thermistor. The temperature sensor 80 is mounted or integrated in the same way as the heating element 70.

In the region of the recess 44, the heating element 70 and the temperature sensor 80 are represented with a dashed line, in order to indicate that the heating element 70 and the temperature sensor 80, in the region of the recess 44, run around said recess 44.

Figure 5:
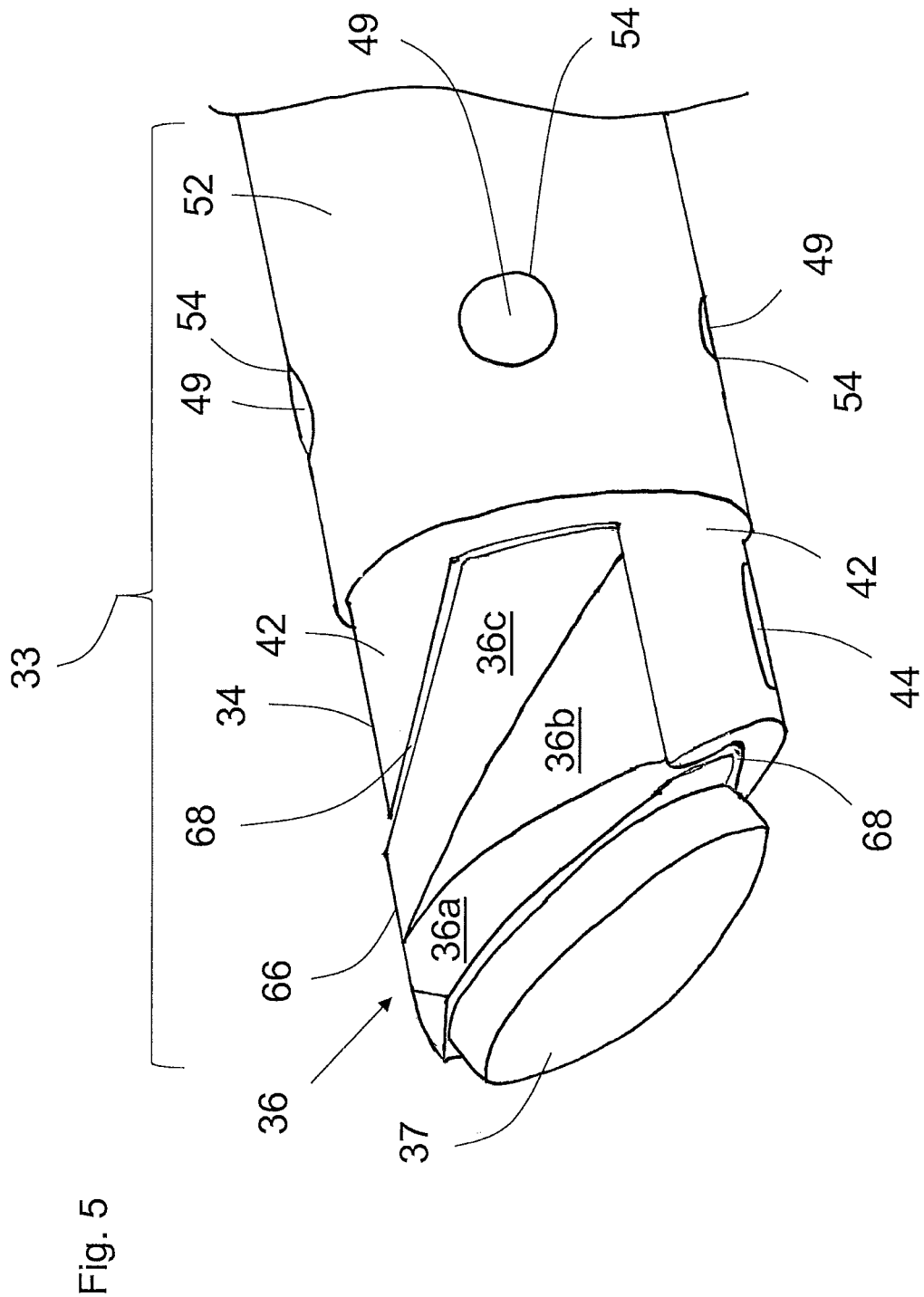
FIG. 5 illustrates a schematically simplified perspective representation of the deflection prism assembly from FIG. 4.

FIG. 5 shows a simplified representation in perspective of the deflection prism assembly 33 from FIG. 4. In this representation, it can be clearly seen that the prism holder 34 only envelopes the deflection prism 36 in certain regions. In addition, the position and the form of the recess 44 and of the recesses 54 are clear. However, the position, number and form of the recesses 44, 54 can differ from the representation in FIG. 5.

The part of the prism holder 34 which is visible in FIG. 5 is the reception component 42 produced from a ceramic, while only the reference points 49 of the internal adjustment component 46 are visible.

Figure 6:
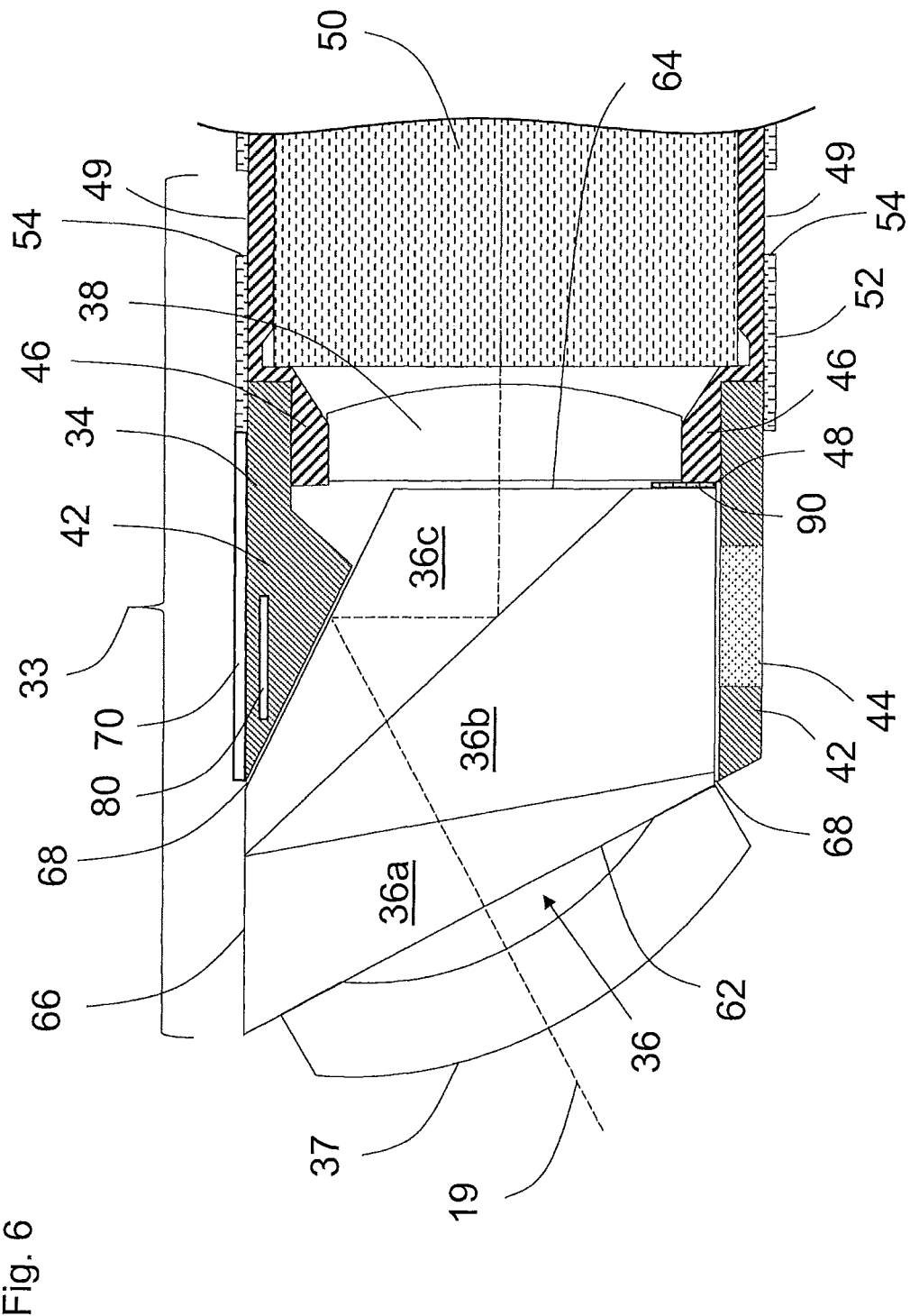
FIG. 6 illustrates a schematically simplified cross-sectional view through a deflection prism assembly having an inlet lens, an outlet lens and a prism holder which comprises a reception component, an adjustment component and a mask.

FIG. 6 shows a further embodiment of the deflection prism assembly 33. In contrast to the embodiment according to FIG. 4, a mask 90 is arranged as a spacer between the stop 48 and the light outlet face 64 of the deflection prism 36 in the embodiment according to FIG. 6. The deflection prism 36 is therefore brought to rest indirectly on the stop 48. Moreover, the heating element 70 is not integrated into the reception component 42 in the embodiment according to FIG. 6, but is arranged on the surface of the reception component 42. Said surface of the reception component 42 is, for example, as shown in FIG. 6, the outwardly directed face of the upper portion of the reception component 42. In addition, the temperature sensor 80 is integrated into the upper portion of the reception component 42 in the embodiment shown in FIG. 6.

While there has been shown and described what is considered to be preferred embodiments, it will, of course, be understood that various modifications and changes in form or detail could readily be made without departing from the spirit of the invention. It is therefore intended that the invention be not limited to the exact forms described and illustrated, but should be constructed to cover all modifications that may fall within the scope of the appended claims.

LIST OF REFERENCE NUMERALS

2 Endoscope
4 Handle
6 Shaft
8 Distal end
10 Inlet window
12 Distal end region
13 Deflection prism assembly
14 Prism holder
16 Deflection prism
16a-16c Sub-prism
17 Inlet lens
18 Outlet lens
19 Beam path
23 Deflection prism assembly
24 Prism holder
26 Deflection prism
26a-26c Sub-prism
33 Deflection prism assembly
34 Prism holder
36 Deflection prism
36a-36c Sub-prism
37 Inlet lens
38 Outlet lens
42 Reception component
44 Recess
46 Adjustment component 48 Stop
49 Reference point
50 Optical system
52 Outer casing
54 Recess
62 Light inlet face
64 Light outlet face
66 Lateral face
68 Adhesive gap
70 Heating element
80 Temperature sensor
90 Mask

What is claimed is:

1. A deflection prism assembly for an endoscope having a lateral viewing direction, the deflection prism assembly comprising:
   a prism holder;
   a deflection prism which is received in the prism holder; and
   at least one electrical heating element for heating the deflection prism;
   wherein the prism holder comprises a reception component and an adjustment component;
   the deflection prism is attached to the reception component and the adjustment component provides a stop for the deflection prism in an axial direction;
   the at least one electrical heating element being disposed in or on the reception component; and
   the at least one electrical heating element at least partially extending in one or more of a circumferential direction or longitudinal direction of the reception component.

2. The deflection prism assembly according to claim 1, wherein the at least one electrical heating element is arranged at least partially on a surface of the reception component.

3. The deflection prism assembly according to claim 1, wherein the at least one electrical heating element extends at least partially within the reception component.

4. The deflection prism assembly according to claim 1, further comprising at least one temperature sensor disposed within or on the reception component.

5. The deflection prism assembly according to claim 1, wherein the adjustment component comprises one or more reference points for radial alignment of the deflection prism.

6. The deflection prism assembly according to claim 1, wherein the deflection prism comprises a light outlet face and an opposite light inlet face arranged diagonally relative to the light outlet face, a lateral face extending between the light outlet face and the light inlet face, wherein the prism holder receives the deflection prism such that the prism holder only surrounds the lateral face of the deflection prism in less than all regions of the lateral face.

7. The deflection prism assembly according to claim 1, wherein the deflection prism is exclusively attached to the reception component.

8. The deflection prism assembly according to claim 7, further comprising an adhesive for attaching the deflection prism to the reception prism.

9. The deflection prism assembly according to claim 8, wherein at least one adhesive gap is disposed between the deflection prism and the reception component, the at least one adhesive gap having a gap width such that no portion of the deflection prism contacts with the reception component.

10. The deflection prism assembly according to claim 1, wherein the reception component is attached to the adjustment component.

11. The deflection prism assembly according to claim 10, further comprising an adhesive for attaching the reception component to the adjustment component.

12. An endoscope having a lateral viewing direction, the endoscope comprising:
    a shaft configured to be inserted into a subject; and
    the deflection prism assembly according to claim 1 disposed in the shaft.

13. A method for assembling a deflection prism assembly, the method comprising:
    attaching an adjustment component to an optical system of an endoscope,
    fitting a reception component onto the adjustment component and attaching the reception component to the adjustment component,
    inserting a deflection prism into a prism holder,
    axially aligning the deflection prism by bringing the deflection prism to rest on a stop of the adjustment component, and
    subsequent to the aligning, attaching the deflection prism to the reception component,
    wherein at least one electrical heating element is arranged in or on the reception component; and
    the at least one electrical heating element at least partially extending in one or more of a circumferential direction or longitudinal direction of the reception component.

14. The method according to claim 13, further comprising radially aligning the deflection prism with an adjustment device by positioning the adjustment device on the deflection prism assembly to interact with reference points of the adjustment component and to lie in contact with at least three regions of the lateral face of the deflection prism.

* * * * *